United States Patent
Vogt et al.

(10) Patent No.: US 8,945,053 B2
(45) Date of Patent: Feb. 3, 2015

(54) INJECTION DEVICE WITH PRICKING PROTECTION AND/OR OVERLOAD PROTECTION FOR A PRODUCT CONTAINER

(75) Inventors: Patrick Vogt, Niederbipp (CH); Ursina Streit, Schönbühl (CH)

(73) Assignee: TecPharma Licensing AG, Burgdorf (CH)

( * ) Notice: Subject to any disclaimer, the term of this patent is extended or adjusted under 35 U.S.C. 154(b) by 439 days.

(21) Appl. No.: 13/305,358

(22) Filed: Nov. 28, 2011

(65) Prior Publication Data

US 2012/0203186 A1  Aug. 9, 2012

Related U.S. Application Data

(63) Continuation of application No. PCT/EP2009/056690, filed on May 29, 2009.

(51) Int. Cl.
*A61M 5/20* (2006.01)
*A61M 5/32* (2006.01)
*A61M 5/00* (2006.01)
A61M 5/46 (2006.01)

(52) U.S. Cl.
CPC .......... *A61M 5/3202* (2013.01); *A61M 5/2033* (2013.01); *A61M 5/326* (2013.01); *A61M 5/3204* (2013.01); *A61M 5/46* (2013.01); *A61M 2005/2013* (2013.01); *A61M 2005/206* (2013.01); *A61M 2005/3215* (2013.01)
USPC .......................... 604/134; 604/192; 604/232

(58) Field of Classification Search
CPC . A61M 5/2033; A61M 5/326; A61M 5/3204; A61M 5/3202; A61M 2005/206; A61M 2005/3261
USPC .......... 604/192–198, 187, 232, 134–136, 208
See application file for complete search history.

(56) References Cited

U.S. PATENT DOCUMENTS

| | | | |
|---|---|---|---|
| 5,658,259 A | 8/1997 | Pearson et al. | |
| 6,960,194 B2 * | 11/2005 | Hommann et al. | 604/198 |
| 8,157,768 B2 * | 4/2012 | Haider et al. | 604/110 |
| 2012/0053528 A1 * | 3/2012 | Bollenbach et al. | 604/192 |

FOREIGN PATENT DOCUMENTS

WO  WO 2007/129324  11/2007

\* cited by examiner

*Primary Examiner* — Rebecca E Eisenberg
(74) *Attorney, Agent, or Firm* — Dorsey & Whitney LLP (57) ABSTRACT

An injection device having a distal end, and including a needle located inside the injection device in an initial position, wherein the needle is moveable to a puncturing position in which the needle projects from the distal end, an open region located distally relative to the needle in the initial position of the needle and having a dimension, and a reduction piece moveable relative to the opening region whereby the dimension may be reduced.

21 Claims, 10 Drawing Sheets

INJECTION DEVICE WITH PRICKING PROTECTION AND/OR OVERLOAD PROTECTION FOR A PRODUCT CONTAINER

CROSS-REFERENCE TO RELATED APPLICATIONS

This application is a Continuation of International Patent Application No. PCT/EP2009/056690 filed May 29, 2009, the contents of which are hereby incorporated by reference.

BACKGROUND

The present application relates to devices for injecting, delivering, administering, infusing or dispensing a substance, and to methods of making and using such devices. More particularly, it relates to an injection device for administering a product, e.g. a drug. In some embodiments, it relates to automatic injection devices, although it is not limited to such devices.

Automatic injection devices, which may be referred to as auto-injectors, are known from the prior art. Such devices provide for automatic delivery of a substance or product. A needle associated with such devices can be injected manually or automatically. If the needle is manually injected or inserted into a patients or users body, the injection movement of the needle is imparted by a user's hand, for example by the user grasping the injection device and pressing it onto an injection point, thus injecting the needle. If the needle is automatically injected, the injection movement of the needle is generated by a drive member, such as a spring element, which advances the needle into the injection point.

Such injection devices can comprise an opening from which the needle can be extended manually or automatically. There are devices in which the opening exhibits a diameter only slightly larger than the needle, such that accessing the needle, for example with a finger, and thus inadvertently pricking oneself is prevented. In these devices, however, the ability to assemble the injection device may be affected or restricted. There are also devices in which the opening is dimensioned large enough to facilitate assembly of the device, but in these devices, the opening is generally large enough that a finger can fit into or through it, thus incurring the danger of an inadvertent needle stick or pricking.

Injection devices which accommodate a product or substance container, e.g. an ampoule, carpoule, vial, etc., containing a product to be delivered are also known. A needle can be attached to the distal end of the product container. In some instances, the proximal end of the product container, i.e. the end opposite the needle, is fastened to the injection device. Due to the forces which arise when an injection device is used, the product container may be released and/or separated from the injection device or, in more extreme cases, the container may break, thus enabling it to fall out of the injection device.

SUMMARY

An object of the present invention is to provide an injection device in which the danger of an inadvertent needle stick or pricking is reduced or eliminated, yet the injection device remains convenient to assemble. (Any reference to "the invention" or "the present invention" in this application shall not be construed as a generalization, limitation or characterization of any subject matter disclosed herein and shall not be considered to be an element or limitation of the appended claims except if and/or where explicitly recited in a claim(s).) Another object of the present invention to provide an injection device in which the product container is prevented from falling out of the device.

In one embodiment, an injection device in accordance with the present invention comprises a distal end, a needle located inside the injection device in an initial position, wherein the needle is moveable to a puncturing position in which the needle projects or extends from the distal end of the device, an opening region relative to the needle in the initial position of the needle and having a dimension, and a reduction piece moveable relative to the opening region whereby the dimension may be reduced. In some embodiments, the opening region is located distally relative to the needle in the initial position of the needle.

In some embodiments, the present invention relates to an injection device for administering a product, e.g. a liquid or fluid product or substance such as a medicinal or therapeutic substance. The product or substance can be stored in a product container in liquid form or in liquid and solid form. In the latter case, the product container may be referred to and/or thought of as a bicameral or multi-chambered product container in which a liquid active agent is mixed with a solid or powdery active agent directly before administering. The injection device can be designed for manual or automatic injecting. In some preferred embodiments, the injection device is an automatic device, which may be referred to and/or thought of as an auto-injector.

In one aspect of the present invention, the injection device comprises a distal end and a needle, wherein the needle is situated within the injection device in an initial position or condition and can be moved to an injection position in which it protrudes or extends beyond the distal end of the injection device. The needle is situated in its initial position in the injection device as sold, shipped or otherwise provided to a user. In the injection position, the needle protrudes beyond the distal end of the injection device to an extent which approximately corresponds to the injection depth of the needle into and/or through the skin at the injection point. The distal end of the injection device is designed to be pressed onto and/or around the injection point. The needle can be fixedly connected to the product container, such as when the product container is manufactured. In this embodiment, the product container can also be referred to as a syringe and its proximal end can comprise a flange by which the syringe can be fastened in the injection device. Alternatively, the needle can be fastened, as a separate part, to the product container. The product container may be referred to as a carpoule or ampoule. The proximal end of the carpoule, ampoule and syringe may, but need not necessarily, comprise a flange for fastening, which is sometimes referred to as a finger flange.

In some embodiments, an injection device in accordance with the present invention comprises an opening region which is situated distally with respect to the needle and/or the needle tip, when the needle is in its initial position, wherein the opening region exhibits a dimension, e.g. a cross-section. When the needle is in its initial position, the opening region can extend between the needle and/or needle tip and the distal end of the injection device. The needle tip is to be understood to mean the distal end region of the needle. The opening region can be surrounded laterally, i.e. around the longitudinal axis of the needle, by a housing or a triggering element, e.g. in the shape of a sleeve. The opening region can exhibit a cross-section, i.e. a cross-sectional area, which is approximately normal to the longitudinal axis of the needle. The cross-section is delineated by the structure or structural element(s) which immediately surrounds the cross-section. The opening region may exhibit a constant or a varying cross-section over its overall axial length. If an opening region comprises a number of cross-sections of different areas, it should be understood that, in some embodiments, it is the smallest cross-section that is being referred to when a cross-section is mentioned.

In some embodiments, an injection device in accordance with the present invention comprises a movable reducing piece. The reducing piece can be moved into the opening region, e.g. from a position which does not lie in the opening region. The movement may be directed along the longitudinal axis, e.g. parallel to the longitudinal axis, transverse to the longitudinal axis, or transverse to and along the longitudinal axis in combination. The movement of the reducing piece into the opening region reduces the cross-section of the opening region. The reducing piece can reduce the cross-section of the opening region at the point at which it is arranged in the opening or open region. The reducing piece may comprise an opening which exhibits a cross-section smaller than the cross-section of the opening region at the point at which the reducing piece is arranged in the opening region. The cross-section of the opening region in the region of the reducing piece may be dimensioned such that the needle can be moved through the opening region despite the reducing piece arranged in the opening region.

Structure, features and function in accordance with the present invention reduce the size of the opening or open region such that accessing the needle through the opening, for example with a finger, is no longer possible. This reduces the danger of inadvertent sticks or pricking, as well as reduces the chance of contaminating the needle.

In some preferred embodiments, an injection device in accordance with the present invention comprises a removing element, e.g. in the form of a cap, which is removably arranged on the injection device, e.g. on its distal end. The removing element prevents access to the needle in the injection device as sold or dispatched. After the removing element is removed from the device, access to the opening region is enabled, yet the opening region is constrictable by the reducing piece, such that access into the opening region up to the needle is not possible.

In some preferred embodiments, the reducing piece can be moved into the opening region from a position in the injection device, e.g. proximally with respect to the needle tip. The product container accommodated in the injection device may comprise a portion which serves to accommodate the product to be administered, wherein the reducing piece can be moved into the opening region from a position which lies axially in the region of the portion for accommodating the product to be administered. The product container comprises a piston which can be moved in the portion for accommodating the product to be administered, e.g. from a proximal position to a distal position. This movement displaces the product and delivers it through the needle. The portion for accommodating the product to be administered lies proximally with respect to the portion to which the needle can be or is fastened.

In some embodiments, the reducing piece may surround the product container partially, e.g. in segments, and in some preferred embodiments it surrounds the container annularly, for example in the region of the portion to which the needle is fastened. The reducing piece may form or comprise a passage for the product container.

In some preferred embodiments, the product container can be provided with a needle protecting cap in the injection device as dispatched, wherein the needle protecting cap is arranged on the portion to which the needle is fastened. The needle protecting cap protects the needle against contamination and keeps it sterile. The product container may be inserted into the injection device as a complete module together with the needle protecting cap. The needle protecting cap may be made of a flexible material, such as a rubber-like material, or a firm material such as hard plastic. The latter embodiment may be referred to as a so-called rigid needle shield. When the removing element and the needle protecting cap are removed, the needle is exposed in the opening region of the injection device, wherein the reducing piece can nonetheless prevent anyone pricking themselves.

In some preferred embodiments, the reducing piece can be fixed in a position in the opening region, such as in a force fit and/or positive fit. An example of a force-fit connection would be clamping the reducing piece in the opening region. An example of a positive-fit connection would be a latching connection in which the reducing piece or a part of the reducing piece latches into an element which surrounds the reducing piece. To this end, in some embodiments the reducing piece can comprise cams or snappers which are elastically biased and latch into the element surrounding the reducing piece at the desired axial position in the opening region. The part which surrounds the reducing piece can comprise one or more recesses into which the reducing piece latches. The part which surrounds the reducing piece can be a housing, a triggering element or a needle protecting sleeve.

In some preferred embodiments, the opening of the reducing piece exhibits a smaller cross-section than the opening region of the injection device and a larger cross-section than a needle protecting cap arranged on the product container and/or a portion for accommodating the product to be administered. This means that during assembly, at least the needle protecting cap of the product container—and, in other embodiments, the portion for accommodating the product to be administered—can be inserted through the opening of the reducing piece.

In some preferred embodiments, the reducing piece can be moved relative to a housing, a needle protecting sleeve, a triggering element and/or the needle. In some embodiments, the needle protecting sleeve can be moved over the needle situated in the injection position to cover the needle again after use. The reducing piece is slaved in the movement of the needle protecting sleeve, e.g. when the reducing piece has been connected axially fixed to the needle protecting sleeve. The triggering element serves to trigger the movement of the needle from its initial position into its injection position. The triggering element can release an energy storage means which shifts the needle, in some embodiments together with the product container. In some preferred embodiments, the needle protecting sleeve can simultaneously perform the function of the triggering element. The needle protecting sleeve which serves as the triggering element can be shifted in the proximal direction relative to the housing, for example by pressing the distal end of the needle protecting sleeve onto the injection point. The needle protecting sleeve or the triggering element can protrude distally beyond the distal end of the housing, wherein when the injection device is pressed onto the injection point, the needle protecting sleeve or the triggering element is moved proximally into the housing. After the injection device has been used, the needle protecting sleeve can protrude beyond the distal end of the housing to an extent which is greater than the extent to which the needle protecting sleeve protrudes beyond the distal end of the housing before the injection is triggered.

Another aspect of the present invention, which can be both pursued in its own right and/or combined with other embodiments of the present invention, relates to an injection device for administering a product which comprises a product container for accommodating the product to be administered. The product container comprises a tapering region or portion which connects distally to a portion for accommodating the product. This portion can be embodied to be hollow-cylindrical and/or can shiftably accommodate a piston which can displace the product from the product container. The piston can be moved through the whole of the portion for accommodating the product. The proximal end of the product container can comprise a projection which extends outwardly, e.g. radially, such as a flange.

In some embodiments, a fastening portion for the needle can connect or be arranged distally with respect to the tapering region of the product container. The fastening portion can be embodied such that a needle can be attached to the product container and/or detached again from the product container. In some embodiments, the needle is fixedly arranged on the fastening portion.

In some embodiments, the needle is exposed at least immediately before administering. In the product container and/or injection device as sold and/or dispatched, the needle can be surrounded by the needle protecting cap which is fastened to the fastening portion for the needle, e.g. in a force fit and/or positive fit, e.g. by being fitted on and/or by a frictional fit. The needle protecting cap can be able to be completely or at least partially removed from the product container to expose the needle. The needle protecting cap can be a so-called rigid needle shield or a simple rubber cap. In the case of a rigid needle shield, it may be possible to remove only a part of the needle protecting cap to expose the needle, wherein another part of the rigid needle shield remains on the product container, e.g. on the fastening portion. The remaining part and removable part of the rigid needle shield can be connected by a material-fit or positive-fit connection, e.g. with a predetermined breaking point, which can be released by being destroyed.

In some embodiments, an injection device in accordance with the present invention comprises a movable holding member which can be moved from a position in which it does not fulfill a holding function for the product container to position in which it does fulfill a holding function for the product container. In some preferred embodiments, the holding member may be moved distally to in front of a tapering region and/or a collar of the product container. The holding member can contact the product container in the position in which it fulfils the holding function, but need not, such that a gap can exist between the tapering region and the holding member as measured in the axial direction. If the holding member contacts the product container, it can serve to divert a force exerted on the product container by removing the needle covering cap. If a gap exists between the holding member and the tapering region, the holding member can serve to prevent the product container from falling out of the injection device if the fastening device with which the product container is normally accommodated in the injection device fails. The fastening device can be embodied by a flange arranged on the proximal end of the product container and/or abutting the proximal end of a product container holder. If the flange should for whatever reason break, the holding member prevents the container from falling out of the injection device.

In some embodiments, the holding member can be shifted from a first position into the holding position. In the first position, the holding member can be situated laterally with respect to the product container, e.g. the portion for accommodating the product. In the first position, the holding member can be arranged such that the tapering region of the product container can be guided past the holding member. In some preferred embodiments, the holding member can be guided at least in portions along the portion for accommodating a product.

In some embodiments, when moving into the holding position, the holding member can be able to perform a radial movement in relation to the longitudinal axis of the product container. To this end, the holding member as a whole or in part can perform a radial movement. The holding member can be deformed, e.g. partially deformed, when it is moved into the holding position. The deformation can be elastic and/or plastic. In some embodiments, the holding member can be pivoted toward the longitudinal axis.

In some preferred embodiments, an injection device in accordance with the present invention comprises a means by which the holding member can perform a combined axial and radial movement when moving to the holding position. Such a means can, for example, be a part of a gear system, a gear surface, a guiding rail, etc. For example, a gear surface can be provided which forces the holding member toward the longitudinal axis of the product container during its axial movement. The gear surface can force the holding member, e.g. shift and/or pivot and/or deform it, at least partially or completely into the holding position.

In some embodiments, the means for deflecting the holding member, e.g. the gear surface, can be arranged or formed on an element which surrounds the product container. This element may be a product container holder. The product container holder can form a passage for the product container; e.g. it can be sleeve-shaped and surround the product container. The holding member is arranged, e.g. radially, between the product container and the product container holder. The product container holder can thus surround both the holding member and the product container. The holding member can be arranged such that it can be moved relative to the product container and/or product container holder when moving into the holding position. The product container holder, the holding member, the product container and the housing of the injection device can, for example, be arranged concentrically with respect to each other.

In some embodiments, the distal end of the product container holder can comprise an opening which allows a part of the product container to be inserted through it. The opening is large enough that the product container, together with a needle protecting cap attached to it, can be inserted through it. The opening can, but need not, be large enough that the portion for accommodating the product to be administered would fit through the opening. The means for deflecting the holding member is arranged on the distal end of the product container holder which is formed over the circumference of the product container holder. The means for deflecting can comprise a surface which is inclined with respect to the longitudinal axis.

In some embodiments, the holding member can surround the product container over its circumference. The holding member can comprise a number of tongues which can be moved to in front of the tapering region of the product container by material deformation. In some preferred embodiments, the tongues can be meant when a holding member which can be moved to in front of the tapering region of the product container is mentioned. This means that not all of the holding member but merely a part of the holding member need be able to be moved to in front of the tapering region. The holding member can comprise an annular base from which the at least one tongue extends, e.g. in the direction of the longitudinal axis.

In some embodiments, in the position in front of the tapering region of the product container, the holding member is or can be latched against moving any further relative to the product container. To this end, the at least one tongue or the annular base or another part of the holding member can comprise a latching element which engages with the part surrounding the latching element, e.g. with the product container holder. The latching element of the tongue can engage with the deflecting means for the holding member and/or tongue.

In some embodiments, an injection device in accordance with the present invention can comprise at least one engaging member which is coupled in a force fit and/or positive fit to at least one of the reducing piece and the holding member, thus enabling the reducing piece and/or holding member to be slaved in an axial movement of the at least one engaging member. In some preferred embodiments, the at least one engaging member can be moved in the distal direction. It can slave the engaging member, at least in portions, in this movement. To this end, the engaging member can comprise links which extend from the annular base, e.g. in the longitudinal direction and in the same direction as the at least one tongue. In some preferred embodiments, the at least one engaging member can be moved in the distal direction and slaves the holding member, at least in portions, in this movement, wherein no relative movement is performed between the holding member and the at least one engaging member in the course of slaving. To this end, the at least one engaging member can engage with the at least one link of the holding member. The holding member and the at least one engaging member can be moved together until the engaging member is moved in front of the product container. It is possible for the at least one engaging member to move further relative to the holding member.

In some embodiments, when the holding member is moved, the reducing piece can be moved along with it by being supported on the holding member. Alternatively or additionally, the reducing piece can be moved along with the at least one engaging member, for example by the engaging member engaging with it. In some preferred embodiments, the needle protecting cap can be removed from the product container when the at least one engaging member is moved in the distal direction, wherein this can be performed before, after or while the reducing piece and/or holding member is slaved.

In some embodiments, the at least one engaging member can be formed on a removing element, e.g. a cap, on one or more arms which extend in the longitudinal direction and mount the at least one engaging member, spring-elastically transverse to the longitudinal axis. The following steps can thus be performed when the removing element is removed from the injection device:

removing the needle protecting cap; and/or
 slaving the holding member, such that its tongues are moved to in front of the collar of the product container; and/or
 slaving the reducing piece into a position in which it reduces the cross-section of the opening region and thus prevents access to the needle.

In some embodiments, an injection device in accordance with the present invention can comprise at least one of the following features:

a needle protecting sleeve which serves as a triggering element for triggering an injection movement of a needle, wherein the needle protecting sleeve can be shifted in the proximal direction relative to the housing of the injection device to trigger the injection movement and can be shifted in the distal direction over the needle situated in the injection position;
 an elasticity means, e.g. a spring, against which the triggering element can be shifted for triggering and with which the triggering element can be shifted in the distal direction over the needle situated in the injection position;
 a driven member which can be shifted in the distal direction by a drive member, e.g. an advancing spring, to shift the product container for an injection movement of the needle and/or to move a piston in the product container for delivering product;
 a blocking member which can be selectively engaged with the driven member or the triggering element to prevent an axial movement of the part with which the blocking member is engaged.

BRIEF DESCRIPTION OF THE DRAWINGS

FIG. 2b is an enlarged view of three parts of the view from FIG. 2a;

FIGS. 3a and 3b are longitudinal sectional views of an injection device with a removing element attached, wherein FIG. 3b is a view rotated by 90° about the longitudinal axis in relation to FIG. 3a;

FIGS. 4a and 4b are longitudinal sectional views of the injection device, from which the removing element has been removed, in an initial state, wherein FIG. 4b is a view rotated by 90° about the longitudinal axis in relation to FIG. 4a;

FIGS. 5a and 5b are longitudinal sectional views of the injection device when triggered, wherein FIG. 5b is a view rotated by 90° about the longitudinal axis in relation to FIG. 5a;

FIGS. 6a and 6b are longitudinal sectional views of the injection device in a state after an injection sequence and before a delivery sequence, wherein FIG. 6b is a view rotated by 90° about the longitudinal axis in relation to FIG. 6a;

FIGS. 7a and 7b are longitudinal sectional views of an injection device after a delivery sequence, wherein FIG. 7b is a view rotated by 90° about the longitudinal axis in relation to FIG. 7a; and FIGS. 8a and 8b are longitudinal sectional views of an injection device comprising a needle protecting sleeve in a needle protecting position, wherein FIG. 8b is a view rotated by 90° about the longitudinal axis in relation to FIG. 8a.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figure 2A:
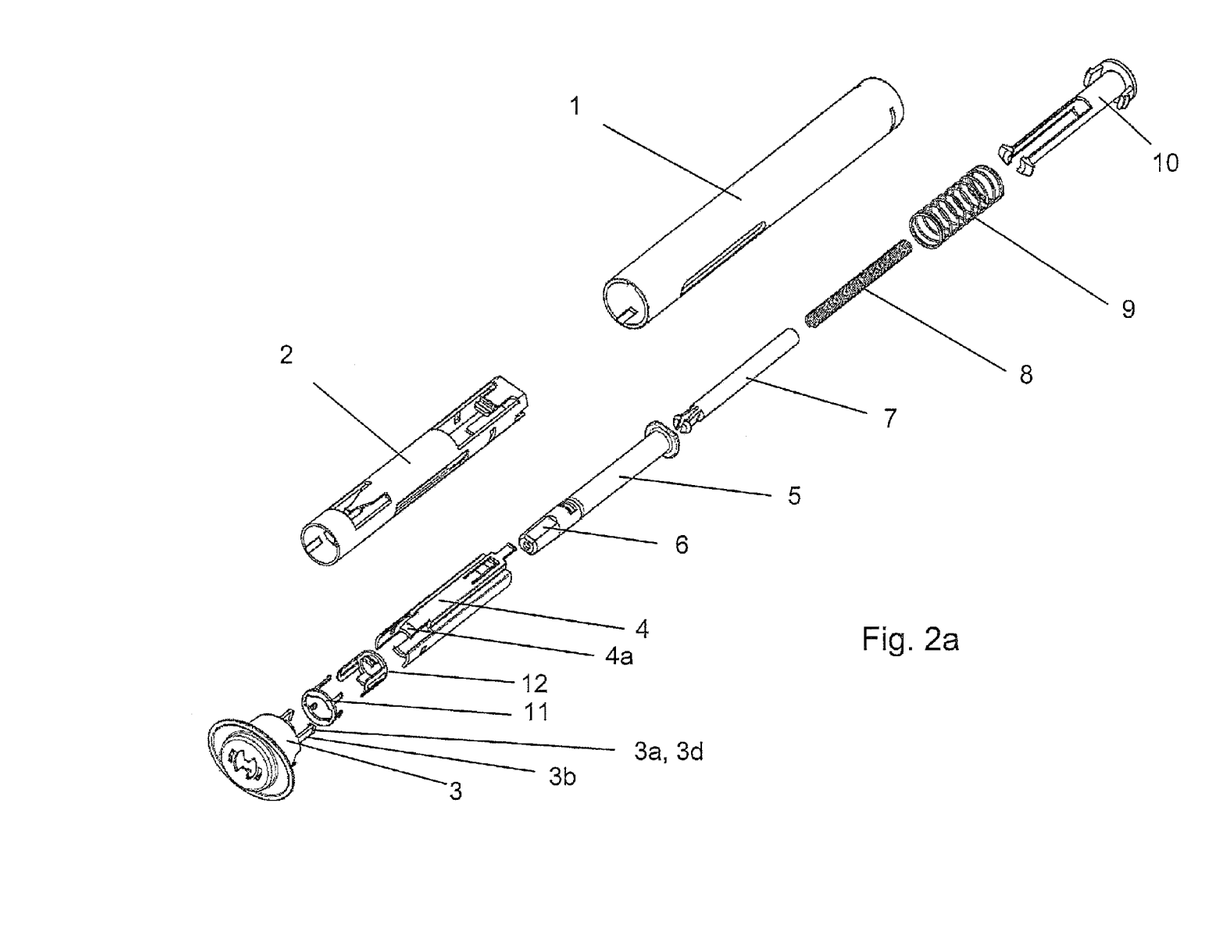
FIG. 2a depicts individual parts of the injection device, in a perspective view.

The individual parts of an injection device, which specifically form an auto-injector, shall firstly be described with reference to FIGS. 2a to 2c. In the depicted embodiment, the injection device comprises: a sleeve-shaped housing 1; a needle protecting sleeve 2 accommodated in the housing 1 such that it can be longitudinally shifted and simultaneously serves as a triggering element; a product container 5 with a needle protecting cap 6 detachably fastened to it; a product container holder 4 which accommodates the product container 5 and comprises deflecting structure or means 4a; a removing element 3 which comprises engaging members 3a, 3d; a drive member 8 in the form of a helical spring which acts as a pressure spring and supplies the energy for injection and delivery sequences; a driven member 7 which acts on the product container 5; a holding element 10 which keeps the drive member 8 tensed until the injection device is triggered and which is connected axially fixed to the housing 1, snapped onto the housing 1; and a spring element 9 which supplies the energy for shifting the needle protecting sleeve 2 to the needle protecting position. The injection device also comprises a holding member 12 which allows easy assembly and can nonetheless prevent the product container from falling out of the injection device, and a reducing piece 11 which serves as an access protection to prevent anyone sticking or pricking themselves on the device. Of preferred embodiments, the one shown here includes both the holding member 12 and the reducing piece 11. In principle, the injection device can be fitted with only one of these two parts.

Figure 1:
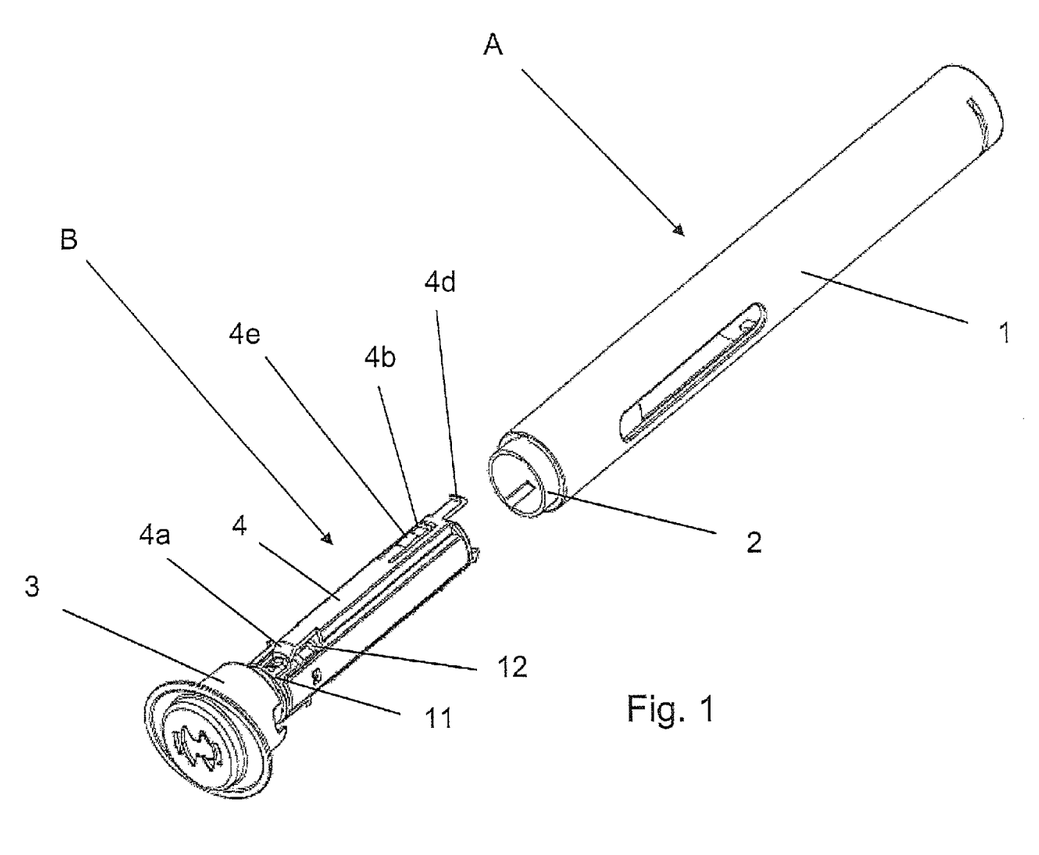
FIG. 1 depicts two sub-assemblies of an embodiment of an injection device in accordance with the present invention, before their final assembly.

FIG. 1 shows an auto-injector before its final assembly. When finally assembled, the auto-injector is provided in two sub-assemblies, namely a sub-assembly A which comprises the housing, the needle protecting sleeve 2 and the drive unit, already biased, and a sub-assembly B which comprises the product container 5, the product container holder 4, the removing element 3 and at least one of the holding member 12 and the reducing piece 11. This division into sub-assemblies has the advantage that the sub-assemblies can be pre-assembled at a location other than the location at which the product container is finally assembled and/or integrated. The sub-assembly A and the sub-assembly B minus the product container can, for example, be supplied from a first facility to a second facility, wherein at the second facility, the product container 5 together with the needle protecting cap 6 is inserted with the needle protecting cap 6 first into the product container holder 4 of a combination of the product container holder 4 and the removing element 3 via an opening on the proximal end of the product container holder 4. The holding member 12 and the reducing piece 11 respectively comprise an opening (which may be thought of and/or referred to as comprising elements 11d, 12d) which is large enough to insert the needle protecting cap 6 of the product container 5 through. The holding member 12 and the reducing piece 11 are respectively arranged in first positions and respectively shifted into second positions only once the removing element 3 is removed from the injection device. This enables the product container 5 including the needle protecting cap 6 to be easily integrated into the rest of the parts of the sub-assembly B.

The completely assembled sub-assembly B can then be inserted into the sub-assembly A via an opening on the distal end of the triggering element 2, where it is fastened to the housing 1, axially fixed but detachably, by a fastening member 4b of the product container holder 4 which in this example is formed as a snapper. Another advantage of the division into sub-assemblies is that a multitude of sub-assemblies A and B can be supplied from the first facility to the second facility, and at the second facility is a decision made as to which drug the injection device is to be fitted with. This increases the ability of the injection device to be flexibly used.

Figure 2B:
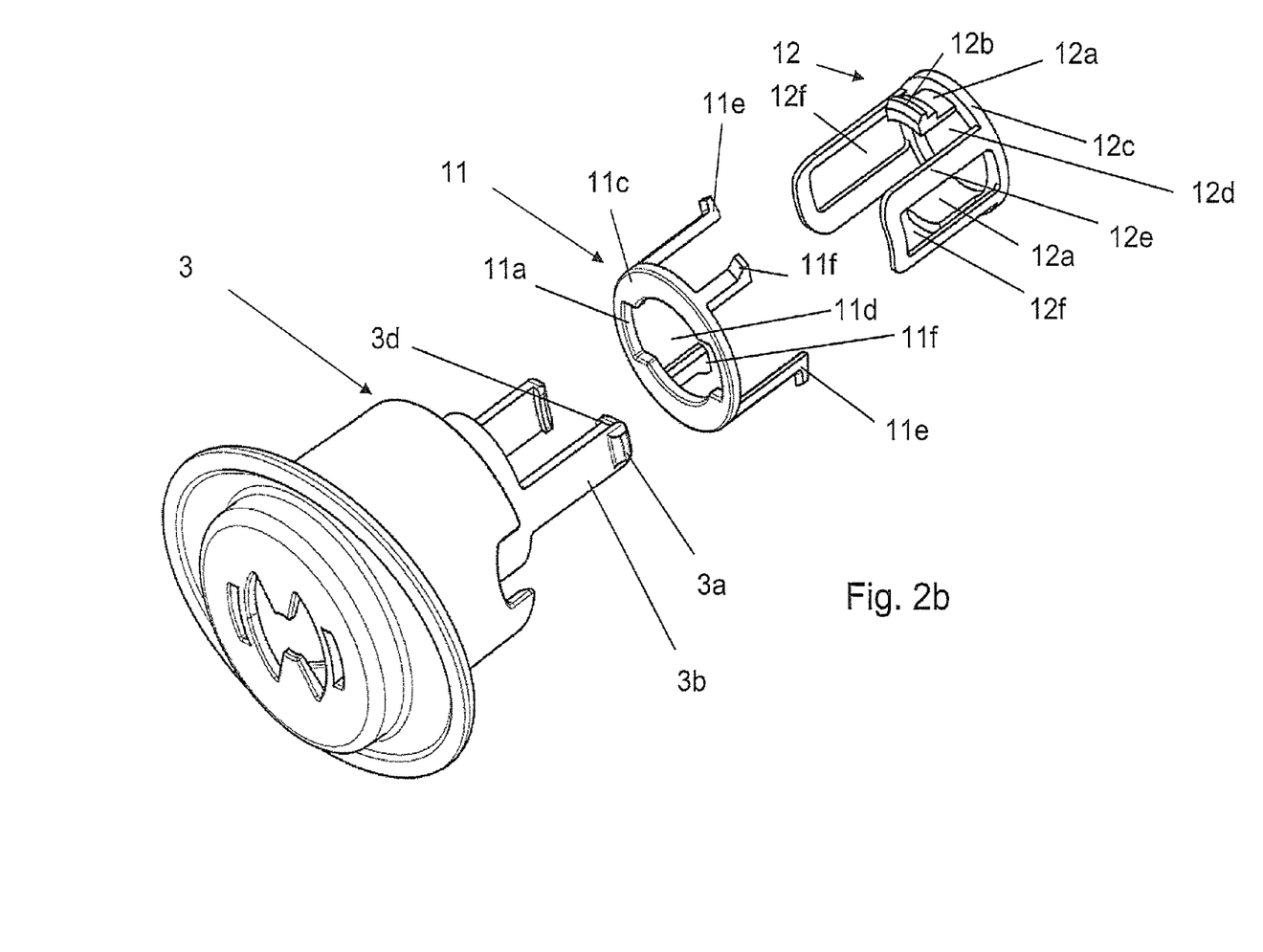
Figure 2C:
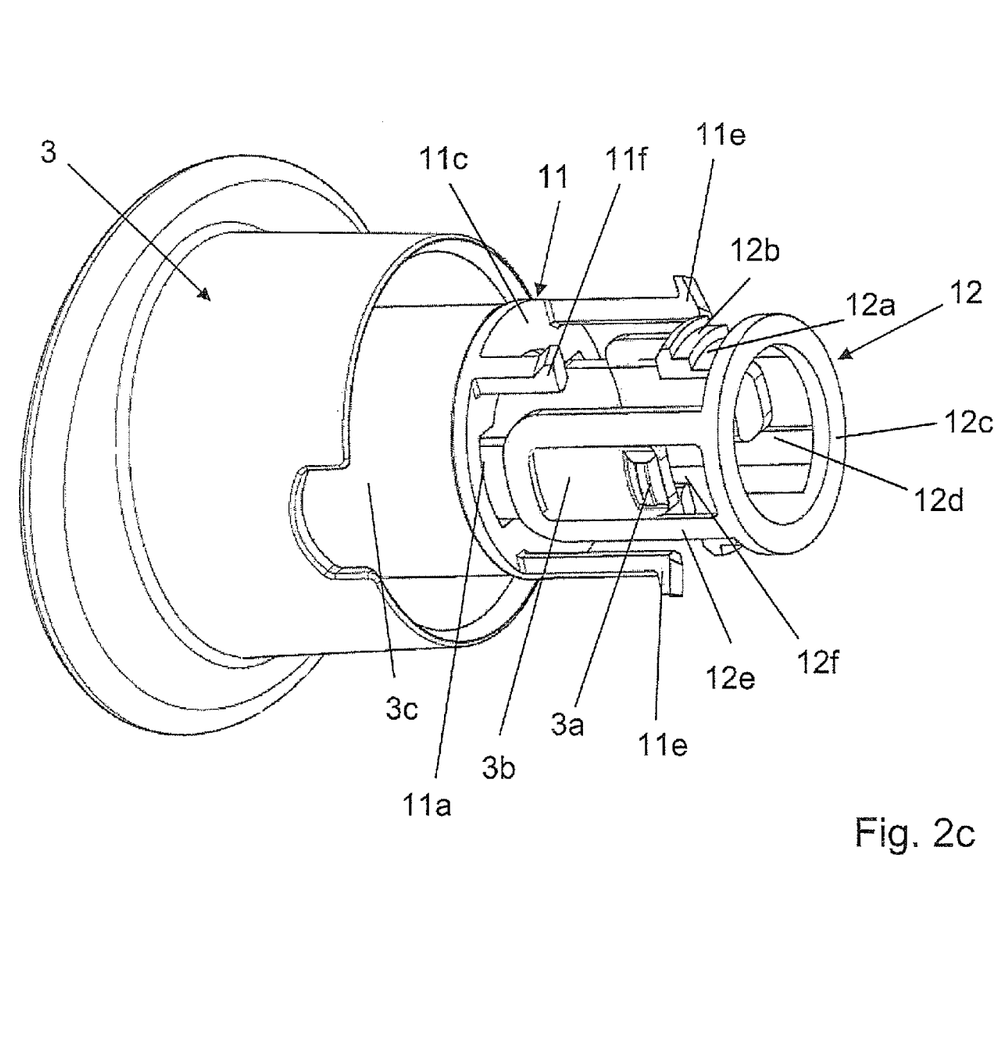
FIG. 2c is an arrangement of the three parts from FIG. 2b, as shipped or sold.
Figure 3A:
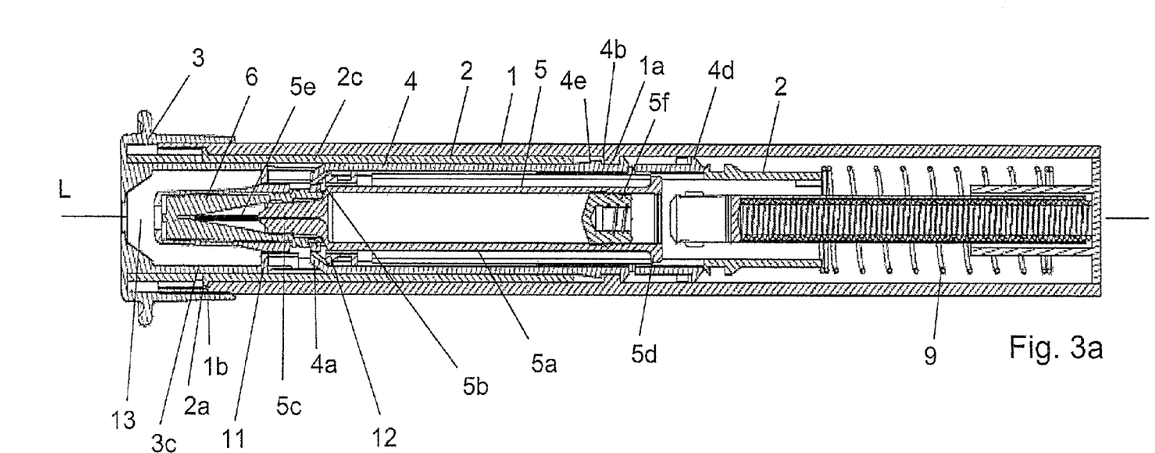
Figure 3B:
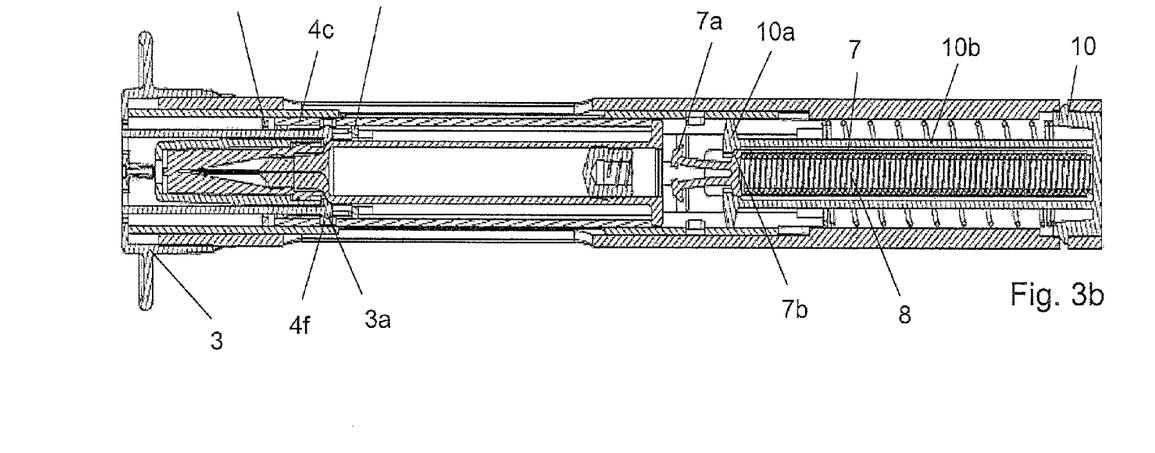

FIGS. 3a and 3b show the completely assembled injection device as sold and/or shipped or dispatched. Reference is additionally made to the representation of the individual parts in FIGS. 2a to 2c. The product container 5 is shiftably mounted in the housing 1. The product container 5 is accommodated in the product container holder 4 such that it cannot be moved in the distal direction relative to the product container holder 4. This is achieved by a finger flange 5d which is formed on the proximal end of the product container 5 and protrudes radially outwardly and acts on the proximal facing side of the product container holder 4. The reservoir part 5a of the product container 5 accommodates the product to be administered. A piston 5f is accommodated in the hollow-cylindrical reservoir part 5a and abuts the inner wall of the reservoir part 5a, forming a seal, and can be shifted in the direction of the needle 5e relative to the reservoir part 5a for delivering product. The needle 5e is non-detachably fastened to a fastening portion 5c of the product container 5. The fastening portion 5c connects distally to the reservoir part 5a. The reservoir part 5a transitions into the fastening portion by a collar 5b. The collar 5b thus forms a tapering region, at or in front of which at least a part of the holding member 12 is subsequently moved. To protect the needle 5e against contamination and to keep it sterile, the needle protecting cap 6 is arranged on the fastening portion 5c and over the needle 5e. The needle protecting cap 6 is fastened to the fastening portion 5c of the product container 5 in a force fit and/or positive fit. Between the collar 5b of the product container 5 and the proximal end and/or proximal facing side of the needle protecting cap 6 there exists a gap which is at least large enough that at least one or both of the engaging members 3a, 3d and a part of the holding member 12 can engage with the gap.

The holding member 12 and the reducing piece 11 are shown in detail in FIGS. 2b and 2c. The reducing piece 11 comprises an annular base 11c. The annular base 11c comprises a passage or opening 11d which is dimensioned such that the needle protecting cap 6 can be inserted and/or moved through it, at least partially or completely. Conversely, the opening 11d is dimensioned such that a human finger does not fit through it. The cross-section of the opening 11d is smaller than the cross-section of the opening region 13 (FIG. 3a), wherein the cross-section of the opening region is reduced by arranging the reducing piece 11 in the opening region 13. The annular base 11c also comprises cavities 11a which are formed laterally with respect to the opening 11d as passages. The cavities 11a can be separate from the opening 11d or—as shown here—connected to the opening 11d. Each of the cavities 11a serves as a passage for an arm 3b which is formed on the at least one engaging member 3a, 3d.

The reducing piece 11 comprises a number of projections which extend in the proximal direction from the annular base 11c and form abutments or latching elements 11e, 11f for the same or different purposes. To this end, the projections can be formed with equal or different lengths.

The latching element 11e can, but need not, serve to abut the holding member 12, e.g. its annular base 12c. The abutment means that when the holding member 12 is moved in the distal direction, the reducing piece 11 is slaved by the holding member 12. If the latching element 11e does not serve as an abutment, the reducing piece 11 can be slaved by the at least one engaging member 3a, 3d.

The latching elements 11e, 11f latch, axially fixed, onto the needle protecting sleeve 2 when the reducing piece 11 is situated in its second position, i.e. in the opening region 13. The reducing piece 11 is slaved in the movements of the needle protecting sleeve 2 due to it latching, axially fixed, onto the needle protecting sleeve 2. In the example shown, the reducing piece 11 comprises two latching elements 11e and two latching elements 11f, wherein the latching elements 11e are formed on projections which are longer than the projections on which the latching elements 11f are formed. The latching elements 11e can serve to block the axial movement in the distal direction, and the latching elements 11f can serve to block the movement of the reducing piece 11 relative to the needle protecting sleeve 2 in the proximal direction. This means, as may be preferred, that the reducing piece 11 is connected to the needle protecting sleeve 2 such that it cannot be moved in either axial direction relative to the needle protecting sleeve 2.

The holding member 12 comprises an annular base 12c from which tongues 12a and links 12e project in the distal direction. The tongues 12a can be deformed or bent toward the central or longitudinal axis of the holding member 12 flexibly, e.g. elastically or plastically. The tongues 12a comprise a latching member 12b on each of their distal ends, which can subsequently latch onto the deflecting means 4a.

Each of the links 12e comprises a groove 12f which extends in the longitudinal direction. The grooves serve to provide an engagement for engaging members 3a or alternatively 3d of the removing element 3. The grooves 12f are continuous but could also be blind grooves. The arms 3b grip through the cavities 11a of the reducing piece 11, such that the at least one engaging member 3a can engage with the groove 12f.

The annular base 12c forms a passage or opening 12d which is large enough that the needle protecting cap 6 can be inserted or moved through it. When not deformed, the latching members 12b do not block the passage for the needle protecting cap 6.

The deflecting means 4a is arranged spring-elastically on the product container holder 4, e.g. by an arm 4g. This arrangement may facilitate assembly. As can be seen from FIG. 1, the product container 5 is inserted into the product container holder 4 which is exposed in the circumferential direction. Since the product container holder 4 is exposed in the circumferential direction before the final assembly, the deflecting means 4a can spring away outwardly and thus let the needle protecting cap 6 through, without an increased assembly force being necessary or there being a danger of clamping. Because the cross-section is latterly reduced by the holding member 12, it is however possible that the deflecting means 4a do not need to spring away, since the passage for the needle protecting cap 6 is initially large enough. The deflecting means does not therefore necessarily need to be arranged spring-elastically but can also be arranged rigidly. When the injection device is finally assembled, as shown for example in FIGS. 3a and 3b, the deflecting means 4a cannot spring outwardly, since the product container holder 4 is surrounded by the needle protecting sleeve 2, wherein the inner side of the needle protecting sleeve 2 forms a holding portion 2c which prevents the deflecting means 4a from moving radially outward.

The product container holder 4 comprises a fastening member 4b, in the form of a cavity, which is directed outward, wherein the fastening member 4b engages with a projection 1a formed on the inner circumference of the housing and thus forms a positive-fit lock. This lock can however be released while using the injection device. The lock means that the product container holder 4 is coupled, axially fixed, to the housing 1, such that the product container 5 also cannot be moved in the distal direction relative to the product container holder 4 due to the engagement of the finger flange 5d onto the proximal facing side of the product container holder 4.

The needle protecting sleeve 2 is guided on the inner circumference of the housing 1. The needle protecting sleeve 2 is situated radially between the product container holder 4 and the housing 1. The needle protecting sleeve 2 can in principle be shifted relative to the housing 1, wherein in the injection device as dispatched, the needle protecting sleeve 2 is axially fixed relative to the housing 1. To this end, the needle protecting sleeve 2 comprises an engaging member 2a which engages in a positive fit with an engaging counter member 1b on the inner side of the housing 1. The engaging member 2a is spring-elastically mounted and can be moved transverse to the longitudinal axis of the injection device. The spring-elastic arrangement is formed by an arm, at the end of which the engaging member 2a is formed.

The removing element 3 at least partially seals the distal end of the injection device. In some embodiments, the removing element 3 prevents access to the needle protecting sleeve 2 which protrudes beyond the distal end of the housing 1. The removing element 3 is fastened to the housing 1 in a force fit, by a sleeve-like continuation which surrounds the distal end of the housing 1. Alternatively or additionally, the removing element 3 can be fastened in a positive fit to the distal end of the injection device, such as for example to the housing 1 or the needle protecting sleeve 2 or via the engagement between the engaging member 3a and the product container holder 4, e.g. its cavity 4f. The removing element 3 also comprises a sleeve-shaped holding portion 3c which in the injection device as dispatched is situated on the inner circumference of the needle protecting sleeve 2, axially level with the engaging member 2a, to prevent the engaging member 2a from moving inwardly, and thus ensures that the needle protecting sleeve 2 is prevented from moving relative to the housing 1 in the injection device as shipped, i.e. with the removing element 3 attached. It is thus possible to reliably prevent the needle protecting sleeve 2 from being moved relative to the housing 1, such as for example when the injection device is dropped and the needle protecting sleeve 2 would be moved relative to the housing 1 due to mass inertia. The engaging member 2a thus serves to provide secure transport. The removing element 3 forms an annular gap between the outer sleeve which is fastened to the circumference of the housing 1 and the inner sleeve which comprises the holding portion 3c. When the removing element is attached, a part of the housing 1 and a part of the needle protecting sleeve 2 are situated in the annular gap, also the engaging member 2a and the engaging counter member 1b formed by the housing. The holding portion 3c, e.g. its proximal end, also forms an assembly aid for pre-assembling the sub-assembly B, for example in that the reducing piece 11, e.g. the annular base 11c, can be supported on the proximal end of the removing element 3 and/or the holding portion 3c, and at least one of the holding member 12 and the product container holder 4 can optionally be supported on the reducing piece 11.

At least one engaging member 3a, 3d is formed on the removing element 3 and can be spring-elastically moved transverse to the longitudinal axis of the injection device via the arm 3b. While the sub-assembly B is pre-assembled, and also in the injection device as dispatched, the cavity 4f formed on the product container holder 4 is situated level with the engaging member 3a in the longitudinal direction, such that the engaging member 3a can spring radially outwardly into the cavity. When the product container 5 is inserted into the combination of the product container holder 4 and the removing element 3 while the sub-assembly B is assembled (FIG. 1), the engaging member 3a springs into the cavity 4f when the needle protecting cap 6 passes the engaging member 3a. The engaging member 3a also springs into the cavity 4f when the product container 5 is completely inserted into the product container holder 4, since in this case, the engaging member 3a abuts the distal end region and laterally abuts the reservoir part 5a of the product container 5. Alternatively, the engaging member 3a or another engaging member 3d can engage with the gap between the needle protecting cap 6 and the collar 5b in this state. The engaging member 3a protrudes radially outward in relation to the outer circumference of the sleeve-shaped portion forming the holding portion 3c and thus forms a gear surface, the function of which is described below.

The engaging member 3d protrudes inwardly in relation to the inner circumference of the sleeve-shaped portion forming the holding portion 3c and is hook-shaped and dimensioned such that it can engage with the gap between the needle protecting cap 6 and the collar 5b in the course of using the injection device.

Since the engaging members 3a, 3d are arranged on approximately the same axial position in the embodiments shown, they can form a common engaging member. In principle, the engaging members 3a and 3d can be arranged on different axial positions.

The removing element 3 also comprises a projection which is directed radially outwardly and makes it easier for the user of the injection device to grip the removing element 3 and apply an axial force to it.

When the product container 5 is completely inserted into the product container holder 4, the projection 5d can abut the proximal end of the product container holder 4 in the longitudinal direction.

Figure 4A:
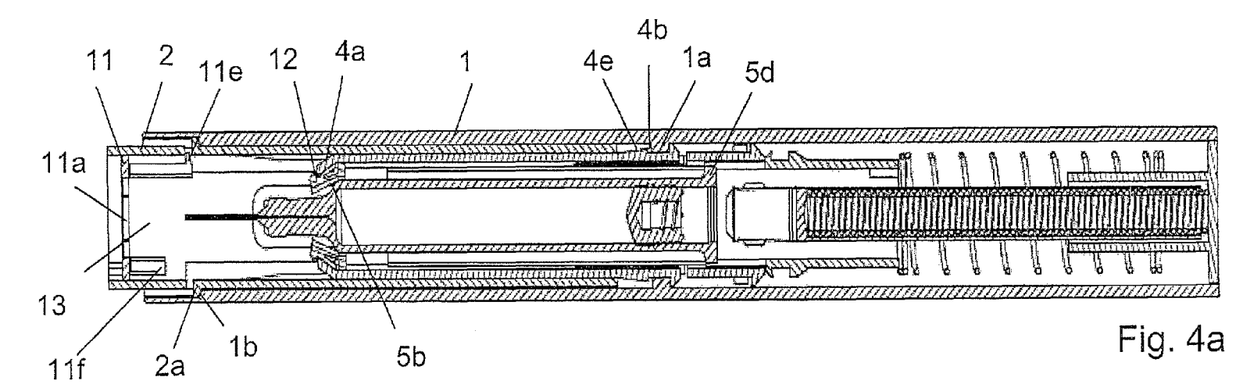
Figure 4B:
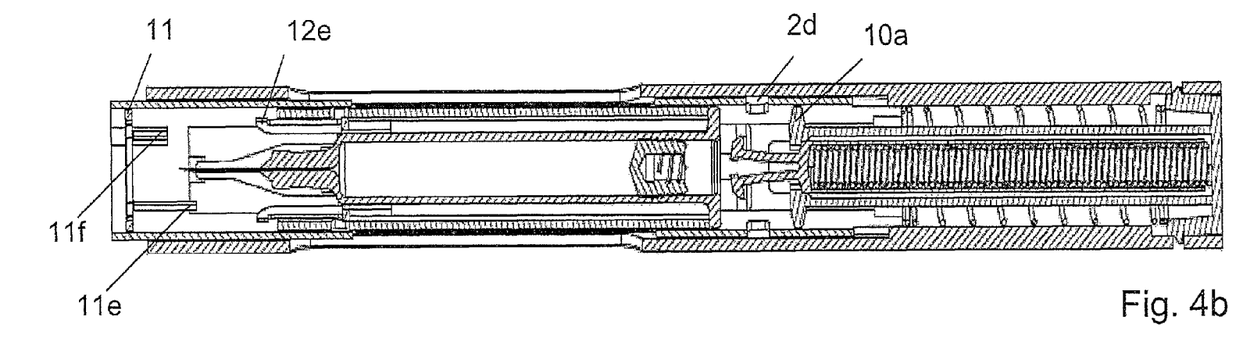

The proximal end of the spring element 9 is supported on the holding element 10 and thus axially fixed with respect to the housing 1, and its distal end 9 is supported on the proximal end of the needle protecting sleeve 2. The spring element 9 is biased and charges the needle protecting sleeve 2 with a force which acts in the distal direction, wherein the needle protecting sleeve 2 is blocked against moving in the distal direction both in the initial position and immediately after the removing element 3 is removed (FIGS. 4a and 4b).

The holding element 10 seals the proximal end of the housing 1 and is connected to the housing 1, e.g. snapped onto it, such that it is axially and rotationally fixed. The holding element 10 could equally be formed integrally with the housing 1, wherein it is advantageous to configure the holding element 10 and the housing 1 in a number of parts, since this facilitates the ability of the individual parts to be manufactured and facilitates assembling the injection device.

The holding element 10 comprises at least one—in this example, two—spring-elastic arms 10b which extend in the longitudinal direction of the injection device and form a blocking member 10a at their distal ends. The blocking member 10a can be moved transverse to the longitudinal axis of the injection device. The blocking member 10a forms an inwardly directed projection and an outwardly directed projection in relation to the arm 10b. The inwardly directed projection engages in a positive fit onto with a collar 7b formed by the driven member 7 and thus prevents the driven member 7 from being moved in the distal direction. The outwardly directed projection of the blocking member 10a abuts an inwardly pointing surface of the needle protecting sleeve 2, such that the blocking member is held in engagement with the collar 7b and prevented from moving radially outward. The proximal ends of the arms 10b are formed on a sleeve-shaped portion of the holding element 10.

The arm 10b extends together with the sleeve-shaped portion of the holding element 10 over the entire length of a sleeve-shaped portion of the driven member 7. The arm 10b, including the blocking member 10a and the sleeve-shaped portion, is longer than the sleeve-shaped portion of the driven member 7. The drive member 8 is accommodated within the sleeve-shaped portion of the driven member 7 in the form of a biased helical pressure spring. The proximal end of the spring element 8 is supported on the holding element 10, and the distal end of the spring element 8 is supported on the distal end of the sleeve-shaped portion of the driven member 7, which simultaneously forms the collar 7b. Two arms which expand in the shape of a fork project from the distal end of the sleeve-shaped portion of the driven member 7 and respectively form a contact element 7a at their distal end. The contact elements 7a comprise bevelled surfaces which are flush with the housing wall of the reservoir part 5a of the product container 5 in the longitudinal direction. This means that the bevelled surfaces of the contact elements 7a enter into abutment with the proximal end of the product container 5 when the driven member 7 moves in the distal direction.

In the following, the function or operation of an embodiment of an injection device in accordance with the present invention is described. Starting from the injection device as dispatched, as shown in FIGS. 3a and 3b, the user of the device grasps the housing 1 with one hand and the removing element 3 with the other hand. To remove the removing element 3, the user pulls on the removing element 3, thus removing it from the housing 1. When the removing element 3 is removed, the engaging members 3d are in or enter the gap between the needle protecting cap 6 and the collar 5b and ultimately enter into abutment with the proximal facing side of the needle protecting cap 6. The engaging members 3a are also moved out of the cavities 4f when the removing element 3 is removed, but remain in the grooves 12f. The engaging members 3a, 3d are ultimately prevented from moving radially outward by the inner side 4c of the product container holder 4, wherein the engaging members 3d are even forced into the engagement with the gap and/or facing side of the needle protecting cap 6. To this end, the engaging member 3a which points radially outward forms a gear surface which slides off on the product container holder 4 when the engaging member 3a moves out of the cavity 4f and thus, with the aid of the holding portion formed by the inner side of the product container holder 4, ensures an engagement between the engaging member 3d and the needle protecting cap 6. When the removing movement of the removing element 3 is continued, the engaging members 3d slave the needle protecting cap 6, thus removing it from the product container 5, and the engaging member 3a latches out of the link 12e or the groove 12f, since the inward supporting effect for the engaging member 3a has been removed. The external force which is introduced into the product container 5 by the removing movement can be diverted from the collars 5b of the product container 5 onto the product container holder 4 via the deformed tongues 12a and from the product container holder 4 into the housing 1 via the engagement 4b. Alternatively or additionally, the external force can be diverted from the finger flange 5d onto the product container holder 4 and from there into the housing 1 via the engagement 4b. In the first alternative, the projection 5d of the product container 5 remains unstressed, thus avoiding damage to the product container 5. When the removing movement of the removing element 3 is continued, the engaging member 3a which has latched out of the groove 12f acts on the annular base 11c and slaves the reducing piece 11. Removing the removing element 3 also enables the engaging member 2a of the needle protecting sleeve 2 to move inwards, since removing the removing element 3 also removes the holding portion 3c.

The engagement between the engaging member 3d and the needle protecting cap 6 additionally ensures that the engaging member 3a remains in the grooves 12f. In the removing movement of the removing element 3, the engaging member 3a abuts against the distal end of the groove 12f. The holding member 12 is slaved by the removing element 3. Due to the abutment between the latching element 11e and the holding member 12, the reducing piece 11 is also slaved out of its first position which it assumes in the completely assembled injection device. When the holding member 12 is slaved and/or moved in the distal direction, the tongue 12a is deflected and/or deformed toward the longitudinal axis by the deflecting means 4a. The deformed tongue 12a is then situated in front of the collar 5b, between the needle protecting cap 6 and the collar 5b. The deformed tongue 12a latches onto the latching member 12b which projects radially outward from the tongue 12a, onto the deflecting means 4a or onto the product container holder 4. The holding member 12 is thus axially fixed relative to the product container holder 4.

The latching elements 11e and 11f of the reducing piece 11, which is slaved by the removing element 3 with the aid of the holding member 12 and/or the engaging member 3a, latches—axially fixed—onto the needle protecting sleeve 2, as shown for example in FIGS. 4a and 4b.

FIGS. 4a and 4b show the injection device from which the removing element 3 has been removed. The device is then ready for use. To this end, the user of the device grasps the housing 1 and presses the distal end of the injection device, which is formed by the needle protecting sleeve 2, onto the injection point. This slides the engaging member 2a out of the engagement with the engaging counter member 1b of the housing 1, such that the engaging member 2a is deflected inwardly. A relative movement is performed between the needle protecting sleeve 2 and the rest of the injection device, in which the needle protecting sleeve 2 is pushed over a gear surface 4e of the product container holder 4 which is embodied in the shape of a ramp, thus releasing the engagement between the product container 4 and the projection 1a of the housing 1, by deflecting the fastening member 4b inward. When the needle protecting sleeve 2 is shifted, the spring element 9 is also tensed by the shifting distance and a cavity 2d which is formed by the needle protecting sleeve 2 is moved so as to be axially level with the blocking member 10a. Inserting the needle protecting sleeve 2 triggers the injection sequence and by extension also the delivery sequence. The needle protecting sleeve 2 can thus also be referred to as the triggering element 2.

Figures 5A, 5B:
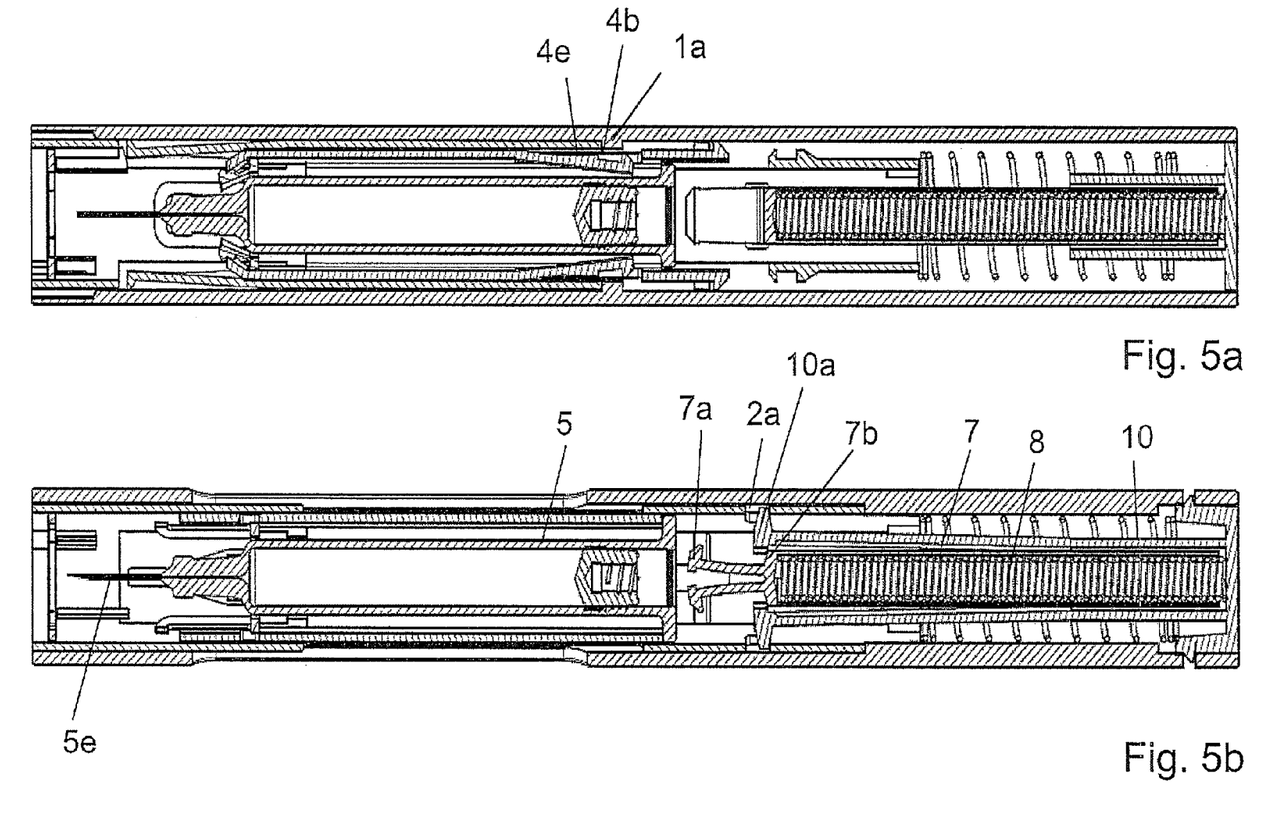

FIGS. 5a and 5b show the injection device in a state in which the needle protecting sleeve 2 has been inserted for triggering. The fastening member 4b is out of engagement with the engaging counter member 1a, thus enabling it to move axially relative to the housing 1.

Figure 6A:
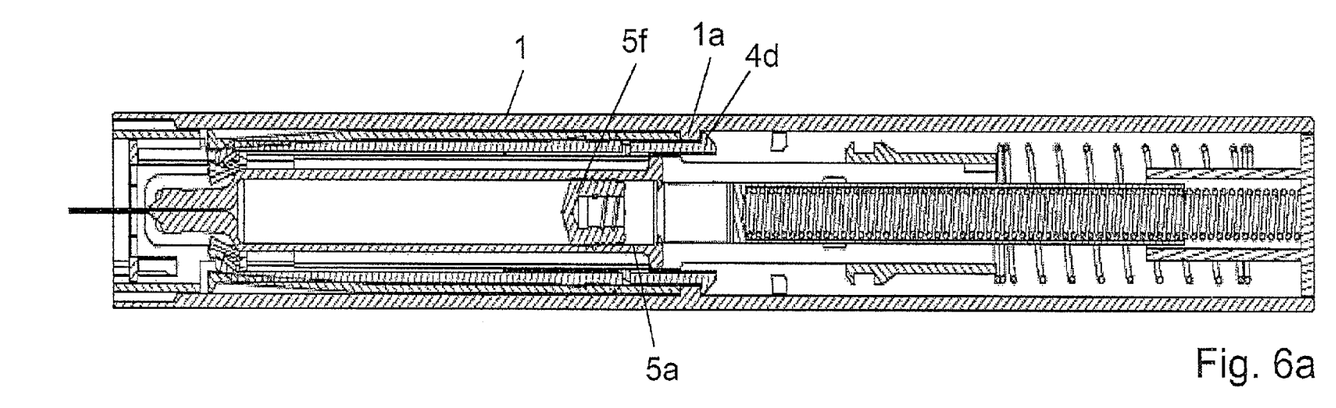
Figure 6B:
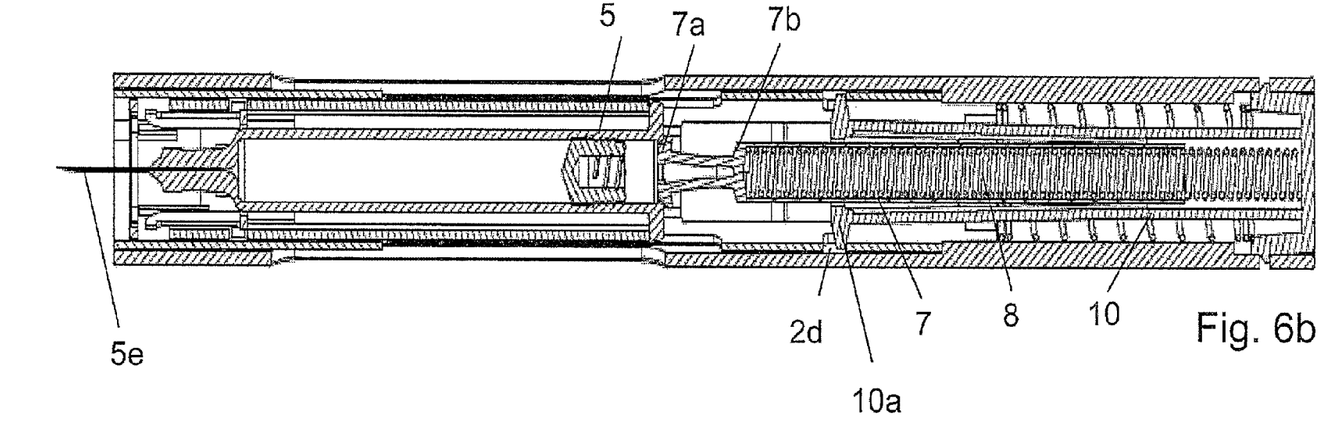

The blocking member 10a can then be deflected into the cavity 2d, wherein when it is in engagement with the needle protecting sleeve 2, it blocks or prevents a movement of the needle protecting sleeve 2 in the distal direction. At the same time as it moves into the cavity 2d, the blocking member 10a releases the collar 7b, such that the biased drive member 8 can move the driven member 7 in the distal direction. The subsequently described part of an overall movement is referred to as the injection sequence. In this movement, the contact elements 7a enter into abutment with the proximal end of the product container 5, thus shifting it in the distal direction until the needle 5e protrudes through the opening 11d beyond the distal end of the injection device in accordance with the desired injection depth, as shown in FIGS. 6a and 6b. As soon as the needle 5e protrudes out of the distal end of the injection device by the corresponding extent, a second fastening member 4d which is formed by the product container holder 4 abuts the projection 1a of the housing 1, thus stopping the advancing movement of the needle 5e. The injection sequence is then complete.

Due to the bevelled surfaces of the contact elements 7a and the force of the drive member 8 which continues to act, the contact elements 7a slide off on the proximal end of the product container 5, such that they are deflected inwardly toward each other and/or into the reservoir portion 5a, and thus enter into abutment with the piston 5f. This starts the delivery sequence, since the force of the drive member 8 shifts the piston 5f in the direction of the needle 5e, such that the substance or product contained in the product container 5 is delivered via the needle 5e.

Figure 7A:
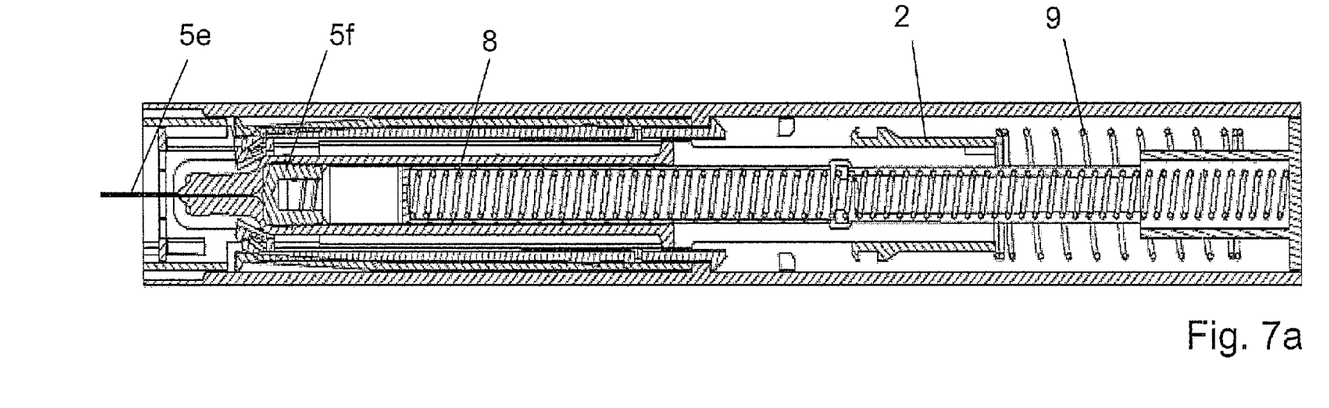
Figure 7B:
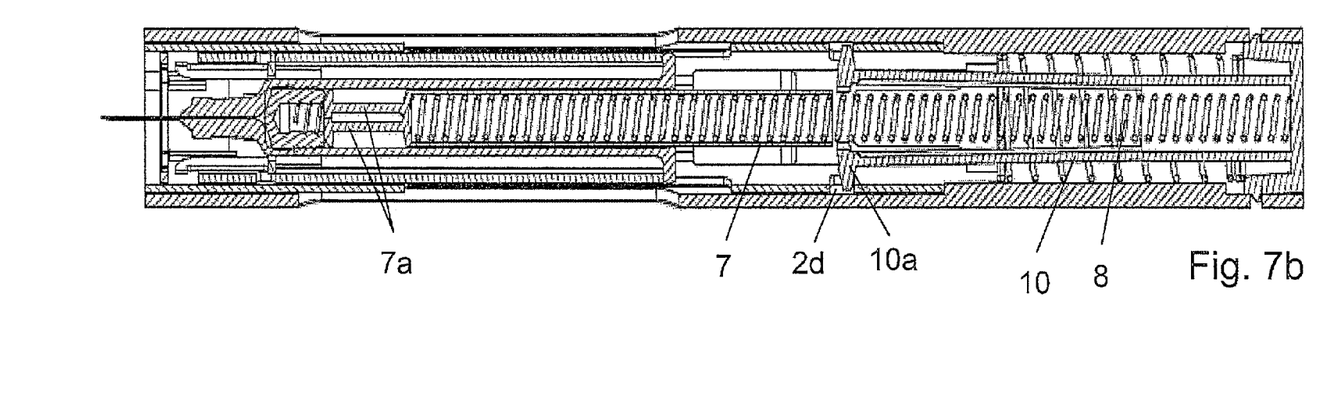

FIGS. 7a and 7b show the injection device at the end of the product or substance delivery sequence, with the contact elements 7a deflected into the reservoir part 5a.

During the injection and delivery sequence, the sleeve-shaped portion of the driven member 7 prevents the blocking members 10a from passing out of the engagement with the cavities 2d of the triggering element 2. At the end of the product delivery sequence, the blocking members 10a can be moved out of the engagement with the cavity 2d, since the driven member 7 has been moved completely past the blocking members 10a.

Figure 8A:
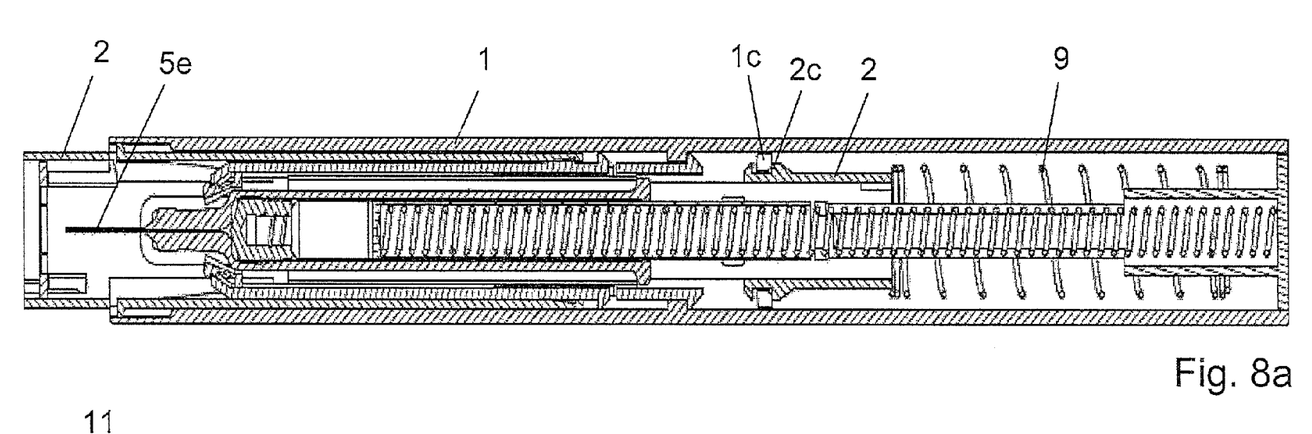
Figure 8B:
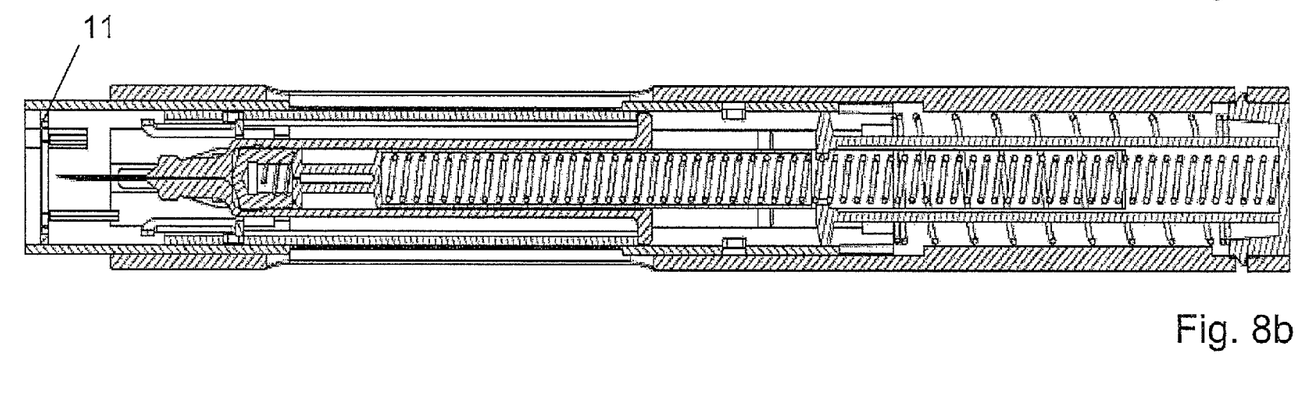

Once the user removes the injection device from the injection point a few seconds after the product delivery sequence is complete, the spring element 9 presses the needle protecting sleeve 2 in the distal direction, wherein the blocking members 10a are moved out of the engagement with the cavities 2d. The needle protecting sleeve 2 is also shifted over the distal end of the needle 5e together with the reducing piece 11, as shown in FIGS. 8a and 8b.

To prevent the needle protecting sleeve 2 from being pushed back into the housing 1, the needle protecting sleeve 2 comprises a blocking member 2c which engages with the projection 1c of the housing 1 in a positive fit, e.g. such that it cannot be released, and/or such that it can only be released by extreme force and/or by being destroyed. It is thus no longer possible under normal circumstances to push the needle protecting sleeve 2 back into the housing 1. It is also not possible to insert a finger into the distal end of the injection device due to the size or dimension, e.g. cross-section, of the opening region 13 being reduced by the reducing piece 11. The danger of injury as a result of using the device is thus reduced.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device for administering a product, comprising a distal end and a needle, wherein the needle is situated within the injection device in an initial position and can be moved to an injection position, the injection device further comprising:

a) an opening region situated distally with respect to the needle when the needle is in the initial position and having a cross-section;
b) a reducing piece moveable into the opening region to reduce the cross-section of the opening region;
c) a needle protecting sleeve which serves as a triggering element for triggering an injection movement of the needle, wherein the needle protecting sleeve can be shifted in a proximal direction relative to a housing of the injection device to trigger the injection movement and can be shifted in a distal direction over the needle situated in the injection position; and
d) an elasticity means against which the needle protecting sleeve can be shifted for triggering and with which the needle protecting sleeve can be shifted in the distal direction over the needle situated in the injection position.

2. The injection device according to claim 1, wherein the reducing piece is moveable into the opening region from a position in the injection device.

3. The injection device according to claim 2, wherein in the position in the injection device the reducing piece is arranged proximally with respect to a needle tip of the needle.

4. The injection device according to claim 1, wherein the reducing piece can be latched in its position in the opening region.

5. The injection device according to claim 1, further comprising a product container containing a portion for accommodating the product to be administered, wherein the reducing piece can be moved into the opening region from a position which is in the injection device and lies axially in the region of the portion for accommodating the product to be administered.

6. The injection device according to claim 5, wherein the reducing piece surrounds the product container.

7. The injection device according to claim 6, wherein the reducing piece is annular.

8. The injection device according to claim 5, wherein the reducing piece comprises an opening which has a smaller cross-section than the opening region and a larger cross-section than a needle covering cap coupled to the product container.

9. The injection device according to claim 1, wherein the reducing piece comprises an opening which has a smaller cross-section than the opening region and a larger cross-section than a needle covering cap coupled to a product container.

10. The injection device according to claim 1, further comprising a housing, wherein the reducing piece can be moved relative to the housing.

11. The injection device according to claim 1, further comprising a product container carried by the injection device, wherein the product container comprises a tapering region, and a movable holding member which can be distally moved to in front of the tapering region of the product container.

12. The injection device according to claim 11, wherein in a first position, the holding member is arranged laterally with respect to a portion of the product container for accommodating a product and can be shifted from the first position to in front of the tapering region of the product container.

13. The injection device according to claim 11, wherein when moving to in front of the tapering region, the holding member performs a radial movement in relation to the longitudinal axis of the product container.

14. The injection device according to claim 11, wherein the injection device comprises a gear surface which forces the holding member radially toward the longitudinal axis of the product container during its axial movement.

15. The injection device according to claim 11, wherein the holding member surrounds the product container over its circumference and comprises a number of tongues which can be moved to in front of the tapering region of the product container by material deformation.

16. The injection device according to claim 11, wherein in the position in front of the tapering region of the product container, the holding member is or can be latched against moving any further relative to the product container.

17. The injection device according to claim 11, wherein the injection device comprises at least one engaging member coupled in a force fit or a positive fit to at least one of the reducing piece and the holding member, thus enabling the reducing piece and/or holding member to be slaved in an axial movement of the at least one engaging member.

18. The injection device according to claim 17, further comprising a removing element removably arranged on the injection device, wherein the removing element forms or comprises the engaging member.

19. The injection device according to claim 18, wherein the removing element is a protective cap.

20. The injection device according to claim 1, further comprising a driven member which can be shifted in the distal direction by a drive member to shift the product container for an injection movement of the needle and/or to move a piston in the product container for delivering product.

21. The injection device according to claim 1, further comprising a blocking member which can be selectively engaged with the driven member or the triggering element to prevent an axial movement of the part with which the blocking member is engaged.

* * * * *